United States Patent

Sippel et al.

[11] Patent Number: 6,129,684
[45] Date of Patent: Oct. 10, 2000

[54] URINE MEASURING DEVICE

[75] Inventors: Martin Sippel, Melsungen, Germany; Rémi Collin, Epernon, France; Karl-Friedrich Voges, Melsungen, Germany

[73] Assignee: B. Braun Melsungen AG, Melsungen, Germany

[21] Appl. No.: 09/387,840

[22] Filed: Sep. 1, 1999

[30] Foreign Application Priority Data

Sep. 2, 1998 [DE] Germany .......................... 198 39 962

[51] Int. Cl.[7] ................................................. A61B 5/00
[52] U.S. Cl. ......................... 600/575; 600/580; 604/322
[58] Field of Search .................................. 600/573, 574, 600/575, 579, 580, 581, 584; 604/317, 318, 322, 323, 324, 325, 329, 349

[56] References Cited

U.S. PATENT DOCUMENTS

| | | | |
|---|---|---|---|
| Re. 30,607 | 5/1981 | Manschot et al. | 600/575 |
| 4,301,813 | 11/1981 | Merry et al. | 600/575 |
| 4,305,403 | 12/1981 | Dunn | 600/575 |
| 4,305,405 | 12/1981 | Meisch | 600/575 |
| 4,622,981 | 11/1986 | Sherlock | 600/575 |
| 4,699,155 | 10/1987 | Villari et al. | 600/575 |
| 4,731,062 | 3/1988 | Gross et al. | 604/322 |
| 4,790,837 | 12/1988 | Gross et al. | 604/322 |
| 4,850,375 | 7/1989 | Rosenberg | 600/575 |
| 5,119,675 | 6/1992 | Mohiuddin | 600/580 |
| 5,409,014 | 4/1995 | Napoli et al. | 600/580 |

*Primary Examiner*—Cary O'Connor
*Assistant Examiner*—Charles Marmor, II
*Attorney, Agent, or Firm*—Diller, Ramik & Wight, PC

[57] ABSTRACT

The urine measuring device comprises a holder (25) to be attached to the bed, which is provided with a measuring container (10) and a collecting bag (33). The measuring container (10) includes an overflow connection (22) which forms, together with the connecting tube (23) of the holder (25), a tube coupling (40). For emptying purposes the measuring container (10) can be swung up about the axis of the tube coupling (40). The urine is then discharged from the measuring container through the overflow connection (22) and the connecting tube (23) of the holder (25) into the collecting bag (33). Subsequently the empty measuring container (10) merely needs to be swung back into its position of use. This facilitates emptying of the measuring container since the container needs not be removed and attached again.

8 Claims, 5 Drawing Sheets

URINE MEASURING DEVICE

BACKGROUND OF THE INVENTION

The invention relates to a urine measuring device for receiving a patient's urine flow and for storing it, e.g. to check the quantity of urine or to provide urine samples.

Urine measuring devices generally comprise a holder to be attached to the patient's bed. To this holder a rigid measuring container is fixed which is connected to a tube coming from the patient's body. The measuring container comprises a measuring chamber or a plurality of measuring chambers which is/are normally transparent and have a measuring scale so that the quantity of urine in the measuring chamber can be read off. From the measuring chamber an overflow leads to a collecting bag. Said collecting bag is exchangeably fixed to the measuring chamber or the holder and can be removed from the holder and emptied, if necessary. Prior to emptying the collecting bag the content of the measuring container should be transferred to the collecting bag. For this purpose the measuring container can be tilted or inclined so that its content flows into the collecting bag. If the known urine measuring devices allow the measuring container to be tilted, the measuring container must, for tilting purposes, first be removed from the holder and then hung in again.

A urine measuring device as known from U.S. Pat. No. 4,850,375 A1 has a normally vertically arranged measuring container that is pivotable for discharging its content into the collecting bag. When the measuring container is swung up, it is emptied into the collecting bag. This process requires a flexible connection between measuring container and collecting bag. The collecting bag is permanently connected to the measuring container so that it cannot be separately exchanged.

U.S. Pat. No. 5,409,014 describes a urine measuring device whose measuring container and collecting bag each comprise a lug to hang them on a hook. A special holder retaining the collecting bag while it is connected with the overflow of the measuring container is not provided. The supply tube coming from the patient's body is connected with the inlet of the measuring container via a plug connection comprising male and female connectors. In a similar way the inlet of the collecting bag is connected with the discharge tube of the measuring container. The measuring container can be tilted for emptying purposes.

SUMMARY OF THE INVENTION

The object of the invention is to provide a urine measuring device which allows the measuring container to be emptied into the collecting bag in a simple manner and which is easy to operate by the hospital personnel.

In the urine measuring device of the invention the overflow connection of the measuring container is connected through a tube coupling with a connecting tube of the holder. Said tube coupling extends along the tilting axis about which the measuring container can be swivelled relatively to the holder. The tube coupling forms a hinge joint which connects the measuring container, independent of its swivelling position, directly with the holder. Thus the measuring container is guided in a defined manner relatively to the holder in each swivelling position with the flow connection between measuring container and connecting tube or collecting bag being maintained. To empty the measuring container the container merely needs to be swung up about its swivelling axis. Then the urine flows from the measuring container through the tube coupling into the collecting bag.

Preferably the frictional force in the swivel joint is adjusted in such a way that the measuring container stops in each position. However, it should be retained by catching or friction at least in its discharge position in which its content is completely drained. After the emptying process the measuring container is swung back into its initial position. It needs not be attached to the hook but just simply hinged down.

Complete evacuation of the measuring container in swung-up position is facilitated when the swivel axis extends transversely to a horizontal line of the holder so that the discharge is in the area of the lowermost location of the swung-up measuring container.

According to a preferred embodiment of the invention it is provided that the measuring container covers or at least partly covers the holder and part of the collecting bag, when it is in its position of use, i.e. swung-down. When the holder is completely covered, only the measuring container and the collecting bag can be seen from the front, i.e. only those parts which need to be checked by the personnel. The holder which has only an auxiliary function and the fastening means for attaching the holder to the bed or any other carrier device are covered. However, the holder is visible and accessible when the measuring container has been swung up.

The measuring container is swung up about a fixed axis of the holder for emptying purposes. This swivel axis preferably extends in parallel to the plane of the holder or that of the collecting bag attached to the holder. However, it is also possible to swivel the measuring container about a swivel axis extending vertically or at a different angle to the plane of the holder.

In a preferred embodiment of the urine measuring device an irreversible catching coupling is arranged along the swivel axis.

Further, the invention relates to an improved coupling of the collecting bag to the holder. For this purpose the holder and the inlet branch of the collecting bag are provided with locking means with the aid of which the inlet branch can be locked at a connecting tube of the holder with the inlet branch being rotated by less than 120° about its axis. The connection between the holder and the collecting bag does not only serve for transferring the fluid but also for carrying the weight of the bag. By locking the inlet branch on the connecting tube a kind of Luer-Lock connection is created which prevents the collecting bag from detaching from the holder owing to the weight of the bag. By combining the carrying and transferring functions in a single part an additional faster on the holder for carrying the bag is not required. Furthermore, exchange of the bag is thus facilitated.

BRIEF DESCRIPTION OF THE DRAWINGS

Hereunder embodiments of the invention are explained in detail with reference to the drawings in which.

DESCRIPTION OF THE PREFERRED EMBODIMENTS

Figure 1:
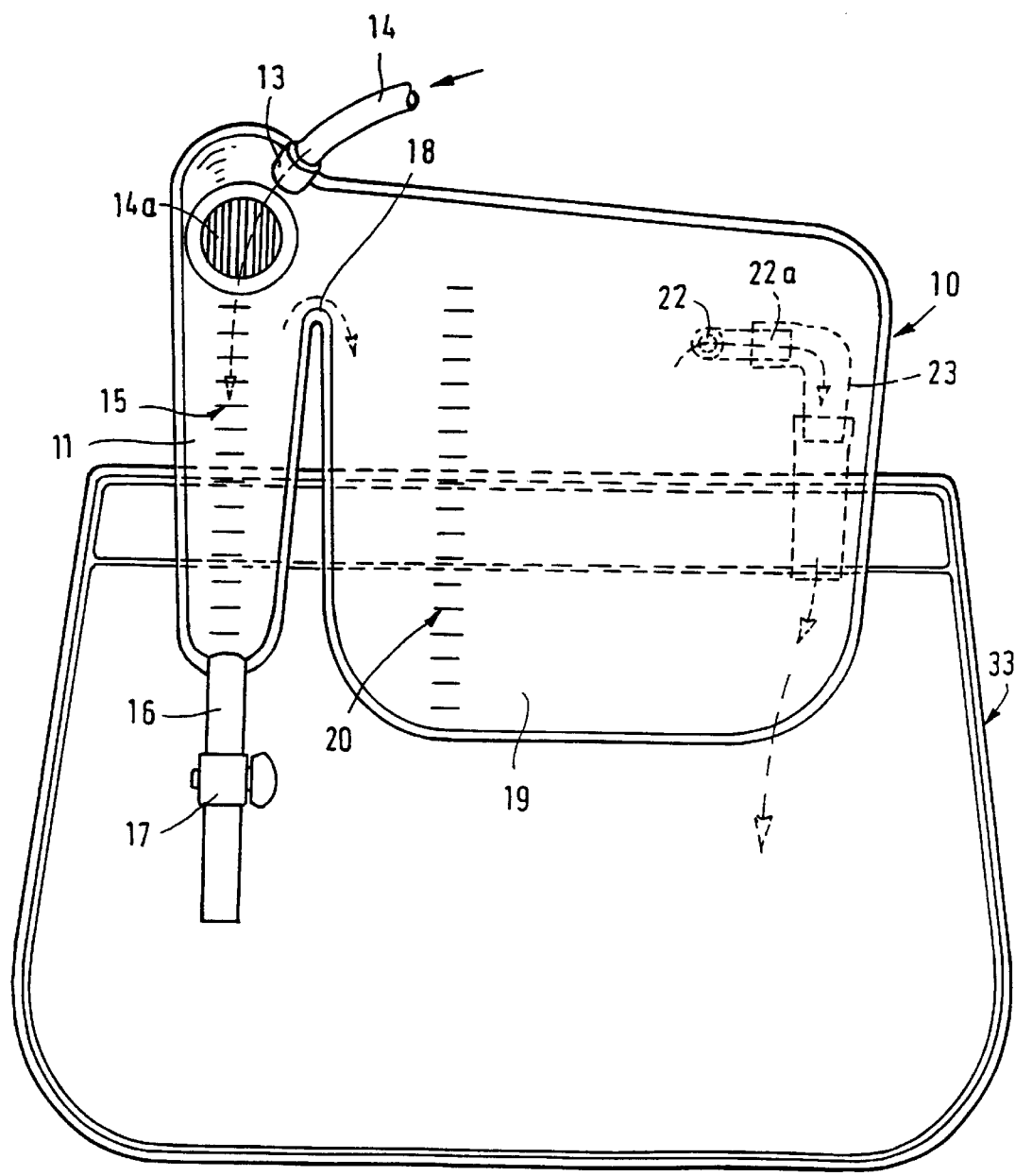
FIG. 1 shows a front view of the urine measuring device.
Figure 2:
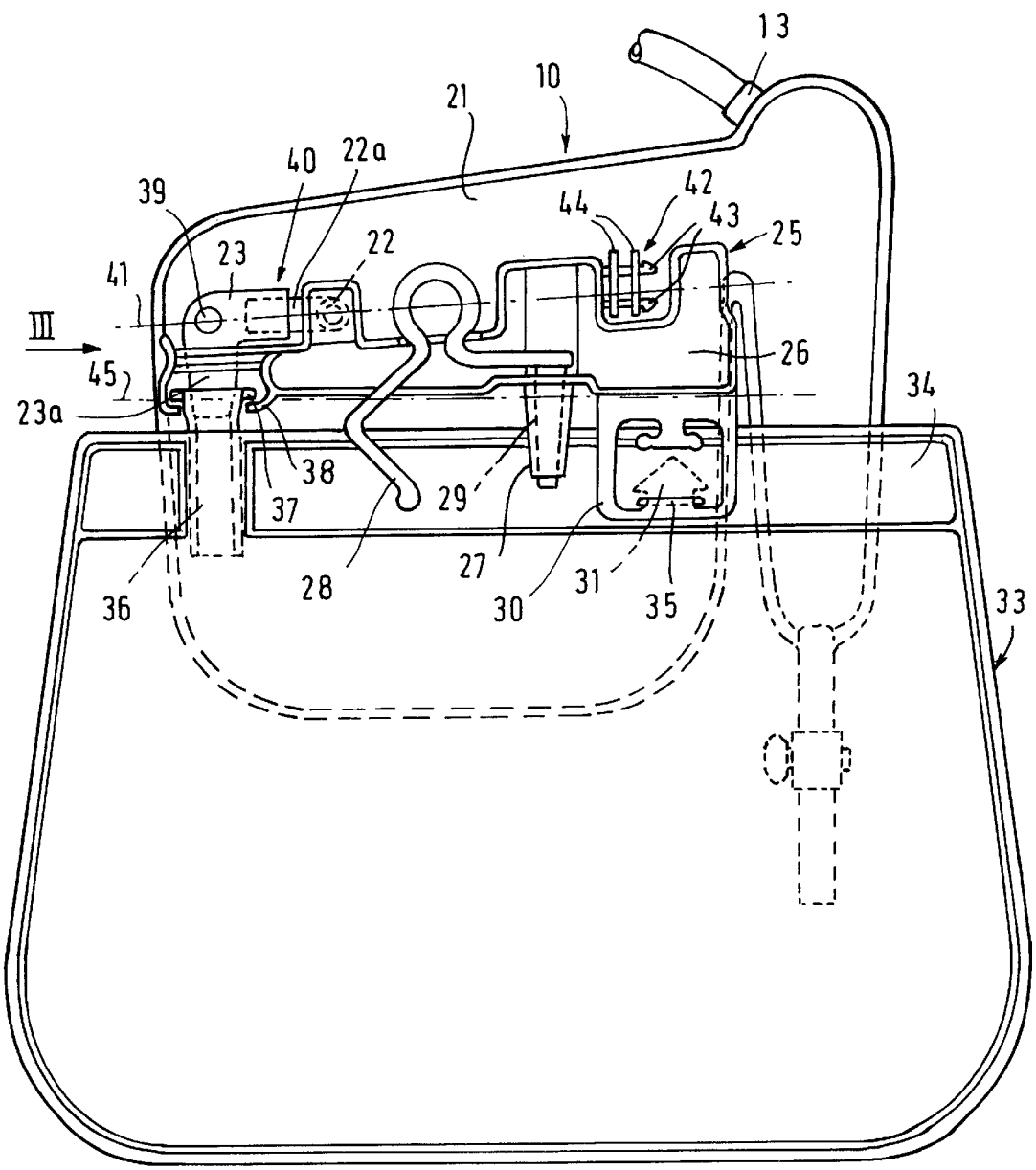
FIG. 2 shows a rear view of the urine measuring device.

The embodiment of the urine measuring device shown in FIGS. 1–4 comprises a measuring container 10 made of plastic material with at least the front side being transparent. The measuring container 10 is a flat container comprising a small first measuring chamber 11 and a larger second measuring chamber 19. A supply connection 13 leads into the first measuring chamber 11; the supply connection being connected with a tube 14 coming from the patient's body. The supply connection is connected with a vent chamber comprising a vent hole 14a. From said vent chamber an overflow leads into the first measuring chamber 11 which is configured as a vertical shaft and comprises a scale 15 indicating the fluid level. To take off urine samples, the lower end of the measuring chamber 11 is provided with a discharge tube 16 having a cock 17.

From the first measuring chamber 11 an overflow 18 leads to the larger second measuring chamber 19. The front wall of said measuring chamber 19 also comprises a scale 20 indicating the fluid level. Both measuring chambers 11, 19 form the measuring container 10.

From the rear wall 21 of the second measuring chamber 19 an overflow connection 22, which forms an integral part of the rear wall 21, leads rearward. Said overflow connection 22 comprises an elbow bent at right angle with a tube section 22a extending in parallel to the rear wall 21.

The measuring container 10 is attached to a holder 25 which can be fastened to a bed, a frame or any other carrier device. According to FIG. 2 the holder 25 comprises a carrier plate 26 with a surrounding reinforcing edge. To said carrier plate 26 a first fastening means 27 in the form of an insert journal and a second fastening means 28 in the form of a flexible hook are attached. The fastening means 28 can be swivelled about its axis 29 engaging in the insert journal. On the bottom side of the holder 25 a hanger fixture 30 in the form of a lug is provided which comprises an upwardly projecting gudgeon 31.

The collecting bag 33 is attached to the connecting tube 23 and the hanger fixture 30 which both form parts of the holder 25. Said bag is a flexible bag made of plastic sheet material which receives the urine discharged via the overflow connection 22 of the measuring container 10. Said collecting bag 33 is provided at its upper end with a reinforcing edge 34 defined by sealing lines. In the reinforcing edge 34 a slot 35 is arranged through which the gudgeon 31 of the hanger fixture 30 is inserted. Further, a tubular inlet branch 36 extends through the reinforcing edge 34. The collecting bag 33 is made of flexible plastic sheet material while the inlet branch 36 is made up of a relatively rigid plastic tube. The inlet branch 36 is placed over the the downward pointing leg 23a of the connecting tube 23. On the outside of the inlet opening 36 locking means 37 in the form of projections and on the holder 25 locking means 38 are provided. Said locking means 37, 38 interact in the form of a Luer-Lock connection and secure the inlet branch 36 against detaching from the tube leg. 23a. The tube leg 23a is configured as outer cone and the upper end of the inlet branch 36 is configured as inner cone. Interlocking is effected by first telescopically placing the inlet branch 36, which is turned by approximately 90°, onto the tube leg 23a until the inlet branch 36 sealingly engages on the tube leg 23a. Then the inlet branch 36 is turned back by 90° with the locking means 37, 38 being brought into the locking condition. This tube connection thus also forms a carrier connection which carries, together with the hanger fixture 30, the collecting bag 33. In the connecting tube 23 a vent means with vent hole 39 for venting the collecting bag 33 is provided.

The tube leg 22a of the overflow connection 22 forms, together with the connecting tube 23 of the holder 25, a tube coupling 40 acting as rotating coupling. The axis of said tube coupling 40 forms the swivel axis 41 about which the measuring container 10 can be swivelled relatively to the holder 25. On the swivel axis 41 a catching coupling 42 is also arranged. The latter comprises resilient gudgeons 43 of the holder 25, which are inserted through rings 44 of the measuring container 10 and catched. The rings 44 can be turned around the gudgeons 43 so that the catching coupling 42 forms a pivot bearing arranged along the swivel axis 41. The swivel axis 41 extends in parallel to the (vertical) plane of the holder 25. When the holder 25 is exactly horizontally aligned, the swivel axis 41 extends at a small angle to the horizontal line 45 with the swivel axis 41 ascending from the tube coupling 40 or the overflow connection 22. The overflow connection 22 is arranged in the measuring container area opposite the supply connection 13.

Figure 3:
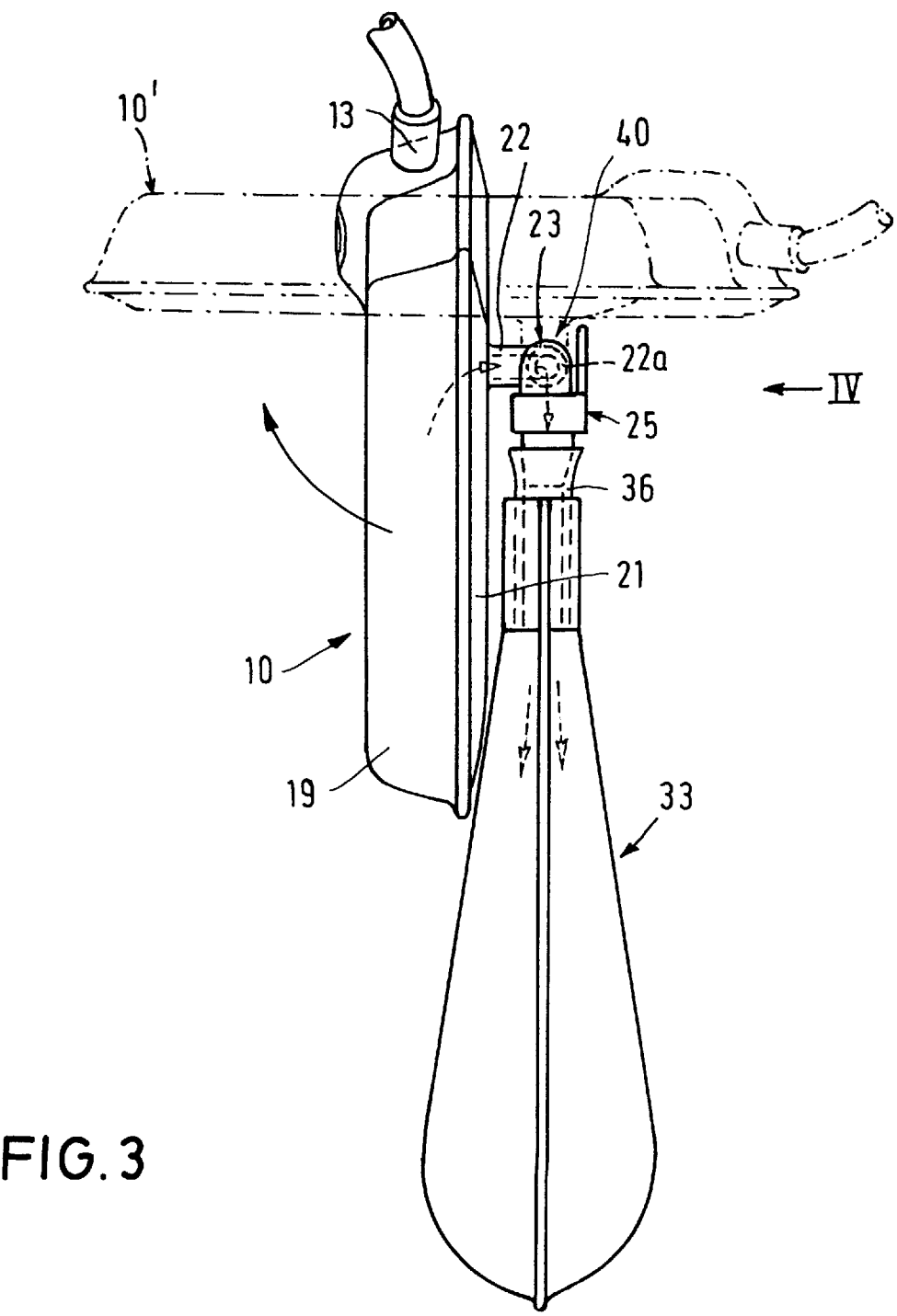
FIG. 3 shows a side view as seen in the direction of arrow III of FIG. 2.
Figure 4:
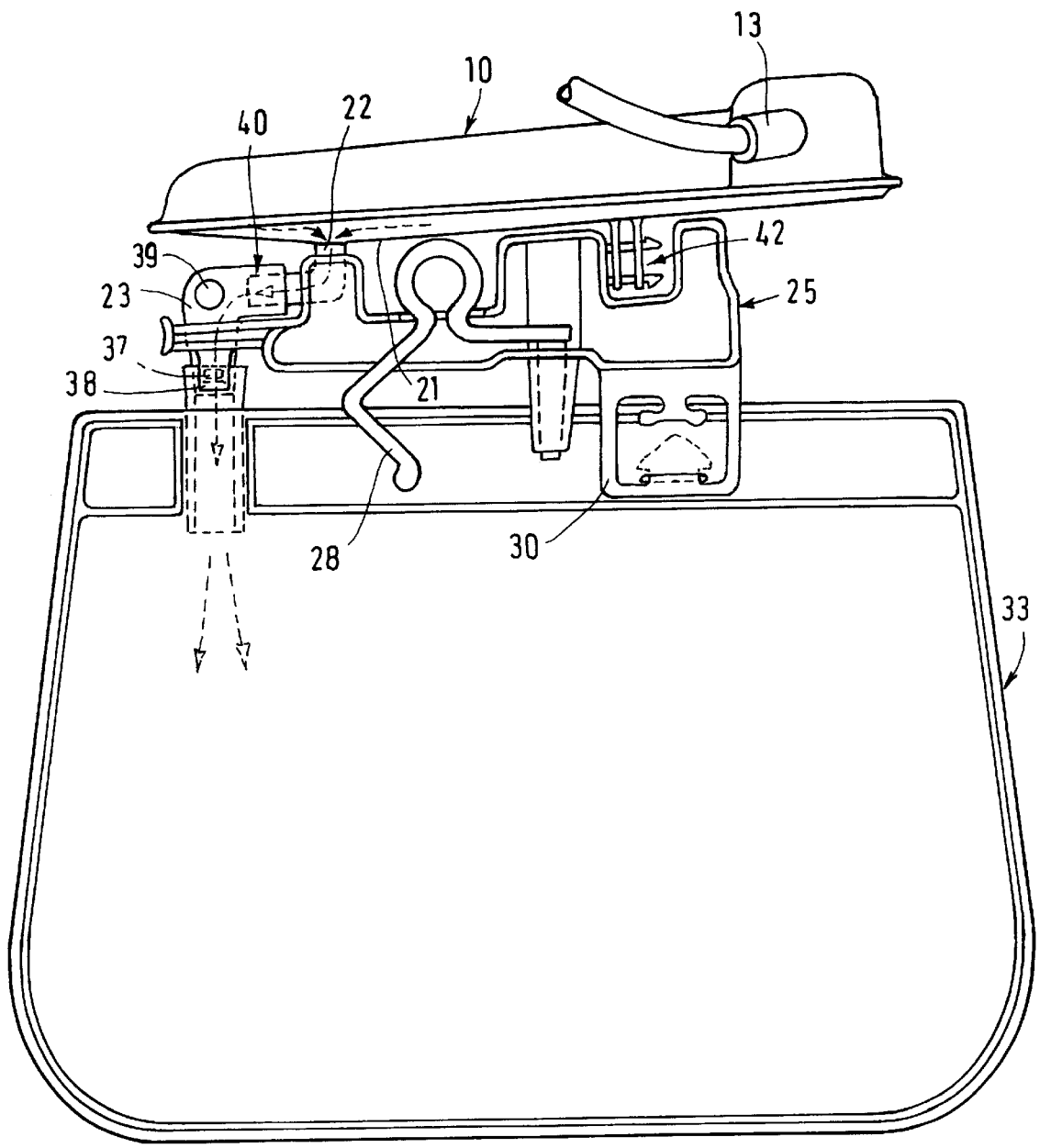
FIG. 4 shows a rear view of the urine measuring device with the measuring container swung up for emptying purposes, as seen in the direction of arrow IV of FIG. 3.

When the measuring container 10 is swung up about the swivel axis 41, as shown by dashed lines in FIG. 3 and continuous lines in FIG. 4, the overflow connection 22 is located at the lowermost position. The rear wall 21 is inclined towards this location. Thus the content of the measuring container 10 can flow to the overflow connection 22, i.e. from the first measuring chamber 11 and the second measuring chamber 19. Then the urine flows through the tube coupling 40 into the connecting tube 23 and from there into the collecting bag 33.

FIGS. 1 and 3 show the position of use of the urine measuring device, in which the urine first flows into the first measuring chamber 11 and from there via the overflow 18 into the second measuring chamber 19. When the second measuring chamber 19 is full, further urine flows through the overflow connection 22 into the collecting bag 33.

To empty the measuring container 10 the container is swung up by approximately 90° so that it assumes the position designated 10' in FIG. 3. In this position the urine is discharged from the entire measuring container 10 through the tube coupling 40 into the collecting bag 33. Then the collecting bag 33 can be taken off the holder 26 and substituted by an empty collecting bag. In the swung-up position the measuring container 10 stops by friction or catching, i.e. it needs not be held in place by the personnel during the discharge process. It is then swung back into the position of use.

Figure 5:
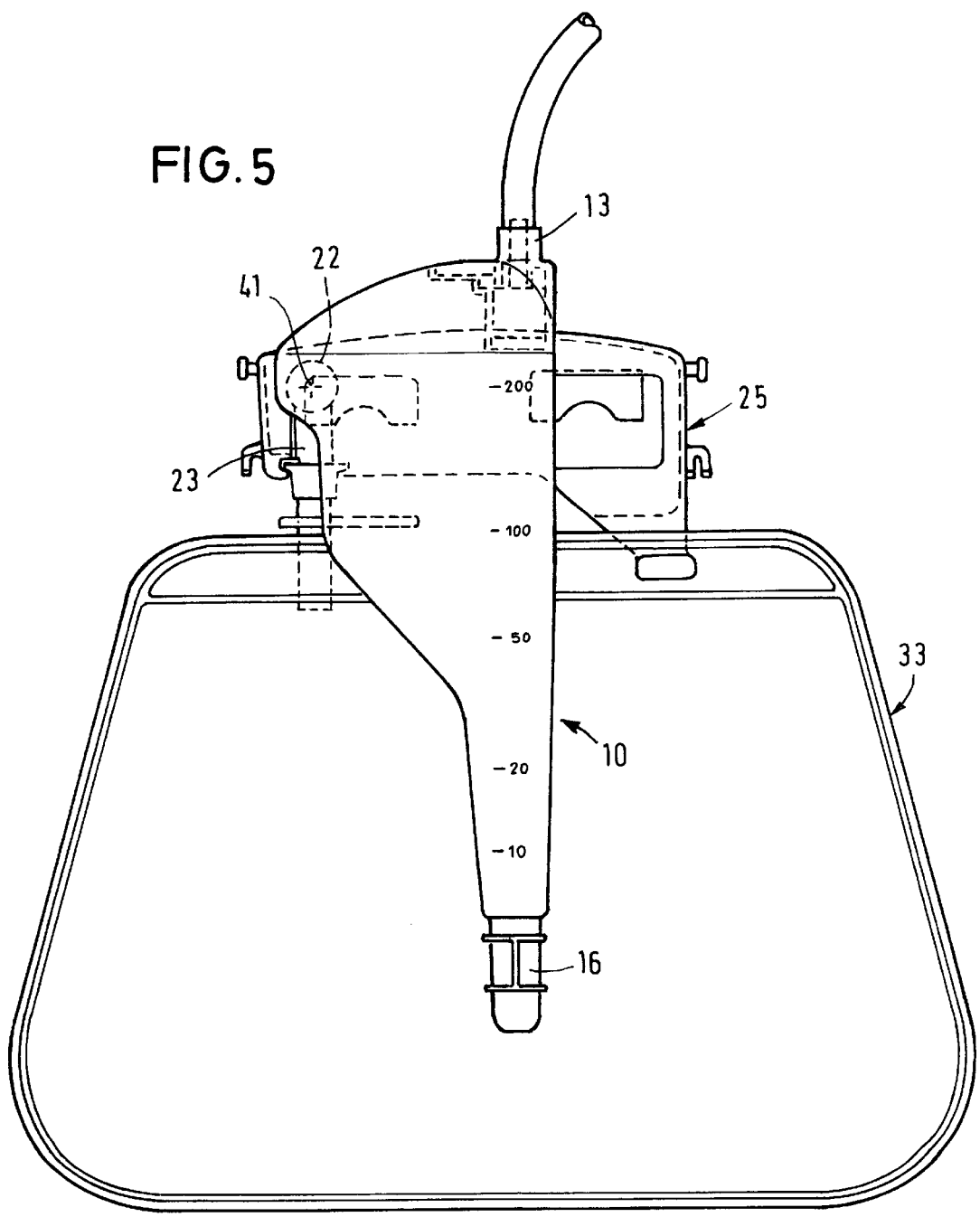
FIG. 5 shows a front view of another embodiment in which the measuring container can be swung up about an axis extending at right angle to the plane of the holder.

In the second embodiment shown in FIG. 5 the measuring container 10 at the holder 25 can be swivelled about the swivel axis 41 which extends substantially horizontally but is aligned vertically to the plane of the holder 25. For emptying purposes the measuring container 10 is thus swung up so that it is positioned in parallel to the plane of the holder 25. The tube coupling extends axially to the overflow connection 22 which is arranged at that location of the measuring container 10 which forms the lowermost location in the swungup condition.

In the embodiment shown in FIG. 5 the measuring container 10 comprises only a single measuring chamber. At the lower end of said measuring chamber a take-off branch 16 for sampling purposes is arranged.

What is claimed is:

1. A urine measuring device comprising a holder (25), a measuring container (10) attached to said holder (25) with the measuring container (10) being provided with a supply connection (13) and an overflow connection (22), and a collecting bag (33) connected with the overflow connection (22) of the measuring container and attached to the holder (25), wherein the measuring container (10) at the holder (25) can be swivelled about a swivel axis (41), a tube coupling (40) being arranged along said swivel axis (41), which rotatably connects the overflow connection (22) of the measuring container (10) with a connecting tube (23) of the holder (25), and the collecting bag (33) being connectable to the connecting tube (23).

2. The urine measuring device according to claim 1, wherein the swivel axis (41) extends transversally to a horizontal axis (45) of the holder (25).

3. The urine measuring device according to claim 1, wherein the measuring container (10) can be swung up by at least approximately 90°.

4. The urine measuring device according to claim 1, wherein, as seen from the front, the measuring container (10), in its position of use, covers the holder (25) and part of the collecting bag (33).

5. The urine measuring device according to claim 1, wherein the swivelling axis (41) extends in parallel to the plane of a carrier plate (26) of the holder (25).

6. The urine measuring device according to claim 1, wherein the connecting tube (23) of the holder (25) comprises a substantially right-angled elbow in which a vent hole (39) is arranged.

7. The urine measuring device according to claim 1, wherein the measuring container (10) is retained by friction or catching in a discharge position.

8. A urine measuring device comprising a holder (25), a measuring container (10) attached to the holder (25) with the measuring container (10) comprising a supply connection (13) and an overflow connection (22), and a collecting bag (33) connected with the overflow connection (22) of the measuring container (10) and attached to the holder (25), wherein the holder (25) and an inlet branch (36) of the collecting bag (33) are provided with locking means (37, 38) by which the inlet branch (36) is lockable at a connecting tube (23) by being turned by less than 120° about its axis.

* * * * *